United States Patent [19]

Susi et al.

[11] 4,052,361
[45] Oct. 4, 1977

[54] N-(2,2-DIMETHYL-6,6-DI(LOWER ALKYL)-4-PIPERIDINYL)-AMIDES OF HINDERED 3,5-DIALKYL-4-HYDROXYBENZOIC ACIDS AND USE AS LIGHT STABILIZERS IN POLYOLEFINS

[75] Inventors: Peter Vincent Susi, Middlesex; John Christian Oppelt, Somerville, both of N.J.

[73] Assignee: American Cyanamid Company, Stamford, Conn.

[21] Appl. No.: 537,152

[22] Filed: Dec. 30, 1974

[51] Int. Cl.² .............................................. C08K 5/34
[52] U.S. Cl. ........................... 260/45.8 N; 260/293.77
[58] Field of Search ................. 260/45.8 N, 293.77

[56] References Cited

U.S. PATENT DOCUMENTS

| | | | |
|---|---|---|---|
| 2,748,134 | 5/1956 | Stoll et al. | 260/293.77 |
| 3,206,431 | 9/1965 | Doyle et al. | 260/45.85 |
| 3,330,859 | 7/1967 | Dexter et al. | 260/473 |
| 3,342,826 | 9/1967 | Miller et al. | 260/293.77 |
| 3,684,765 | 8/1972 | Matsui et al. | 260/45.8 |
| 3,705,166 | 12/1972 | Murayama et al. | 260/293.86 |
| 3,745,163 | 7/1973 | Holt et al. | 260/293.76 |
| 3,993,655 | 11/1976 | Rasberger et al. | 260/293.64 |

Primary Examiner—Donald E. Czaja
Assistant Examiner—R. A. White
Attorney, Agent, or Firm—Philip Mintz

[57] ABSTRACT

Compounds of the formula:

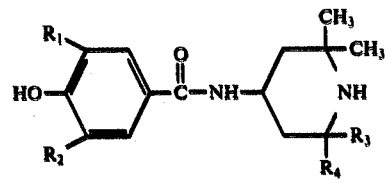

wherein $R_1$ and $R_2$ are each branch-chain alkyl of 3 to 8 carbon atoms and $R_3$ and $R_4$ are each alkyl of 1 to 4 carbon atoms are useful as light stabilizers in polyolefins. They may be prepared by reacting 3,5-dialkyl-4-hydroxybenzoic acid with 4-amino-2,2-dimethyl-6,6-di(lower alkyl)piperidine in the presence of a carbodiimide as dehydrating agent.

10 Claims, No Drawings

N-(2,2-DIMETHYL-6,6-DI(LOWER ALKYL)-4-PIPERIDINYL)-AMIDES OF HINDERED 3,5-DIALKYL-4-HYDROXYBENZOIC ACIDS AND USE AS LIGHT STABILIZERS IN POLYOLEFINS

This invention relates to stabilizing polyolefins against the deteriorating effects of light by the use of certain amides of hindered 3,5-dialkyl-4-hydroxybenzoic acids.

As is well known, polyolefins such as polypropylene and polyethylene tend to deteriorate from the effects of light, especially ultraviolet light. This deterioration generally manifests itself as a loss of tensile strength and loss of flexibility of the polymer. In accordance with the present invention, we have discovered that certain amides of hindered 3,5-dialkyl-4-hydroxybenzoic acid can significantly retard or inhibit such deterioration.

The amides of hindered 3,5-dialkyl-4-hydroxybenzoic acid useful for the practice of the present invention include those having the formula:

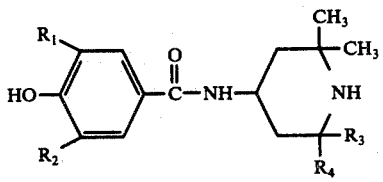

wherein $R_1$ and $R_2$ are each branched-chain alkyl of 3 to 8 carbon atoms and $R_3$ and $R_4$ are each alkyl of 1 to 4 carbon atoms. Illustrative of the branched-chain alkyl moieties from which $R_1$ and $R_2$ may be separately selected are isopropyl, t-butyl, iso-hexyl, cyclohexyl, 2-ethylhexyl, t-octyl, etc. It is preferred for both $R_1$ and $R_2$ to be t-butyl because of the commercial availability of 3,5-di-t-butyl-4-hydroxybenzoic acid, an intermediate from which the amides of the present invention can be prepared. Illustrative of the alkyl moieties from which $R_3$ and $R_4$ may be separately selected are methyl, ethyl, propyl, and butyl. Preferably, $R_3$ and $R_4$ are each methyl because of the commercial availability of 4-amino-2,2,6,6-tetramethylpiperidine, an intermediate for preparing the amides of the present invention.

These new compounds can be prepared in several ways from 3,5-dialkyl-4-hydroxybenzoic acid or its acid chloride. Briefly, one such preparation involves the reaction of the acid chloride with the appropriate amine in the presence of an acid acceptor. Another such preparation involves the condensation of the acid with the appropriate amine in the presence of a carbodiimide as dehydrating agent.

The 3,5-dialkyl-4-hydroxybenzoic acid chloride can be prepared by reacting the corresponding benzoic acid with thionyl chloride in the presence of a catalyst, such as pyridine. The benzoic acid may be purchased (especially the 3,5-di-t-butyl-4-hydroxybenzoic acid) or may be prepared by oxidation of the corresponding aldehyde; see Yohe et al., J. Org. Chem., 1289 (1956) as explained in U.S. Pat. No. 3,206,431 col. 3, lines 32-35. The acid and acid chloride are also described in U.S. Pat. No. 3,330,859 (Examples 3, 5, and 6).

The 4-amino-2,2-dimethyl-6,6-di(lower alkyl)piperidine can be prepared from the corresponding 4-oxo-2,2-dimethyl-6,6-di(lower alkyl)piperidine by reacting it with hydroxylamine to form the corresponding 4-hydroxyimino-2,2-dimethyl-6,6-di(lower alkyl)piperidine which can then be reduced with sodium in amyl alcohol to the 4-amino-2,2-dimethyl-6,6-di(lower alkyl)piperidine. The 4-oxo-2,2-dimethyl-6,6-di(lower alkyl)piperidine can be prepared by the process of U.S. Pat. No. 3,513,170. The 4-amino-2,2,6,6-tetramethylpiperidine can also be purchased commercially.

The compounds of this invention are useful for protecting polyolefins, such as polypropylene and polyethylene, against the deteriorative effects of ultraviolet light when used in amounts of about 0.1 to about 2.0 percent by weight, preferably of about 0.2 to about 1.0 percent by weight, on weight of polymer. These compounds may be incorporated into the polyolefin by any of the standard techniques used in industry, such as by milling, extrusion, swelling into the polymer, etc. Other additives, such as processing antioxidants, secondary stabilizers, pigments, dyes, flame retardants, lubricants, plasticizers, etc. may also be included in the polyolefin for their usual purposes.

For further illustration of this invention, reference should be made to the following examples.

EXAMPLE 1

To a stirred solution of 25 grams (0.1 mole) of 3,5-di-t-butyl-4-hydroxybenzoic acid and 15.6 grams (0.1 mole) of 4-amino-2,2,6,6-tetramethylpiperidine in 100 milliliters of dry tetrahydrofuran was added dropwise a solution of 20.6 grams (0.1 mole) of dicyclohexylcarbodiimide in 75 milliliters of dry tetrahydrofuran. The mixture was stirred for several hours and the white solid (dicyclohexyl urea) was filtered off and discarded. Evaporation of the filtrate gave a white solid, which was recrystallized from 1:1 benzenehexane to give N-(2,2,6,6-tetramethyl-4-piperidinyl)-3,5-di-t-butyl-4-hydroxybenzamide; melting point 256°–258° C.

EXAMPLE 2

Testing in Polypropylene

The compound of Example 1 (0.5% by weight) was milled into unstabilized polypropylene along with 0.2% by weight of a thermal antioxidant, 2,4,6-tri-t-butylphenol. The milled composition was then compression molded into a film 4 mils thick. The compression molded film, and a control film identically prepared except without the compound of Example 1, were exposed in a Fade-Ometer until they failed. The samples were considered as having failed when the carbonyl content in the film, as measured in the infra-red spectrum, reached 0.1%. This carbonyl content generally results in film embrittlement. The test sample lasted 3,400 hours, about 11.3 times as long as the control.

What is claimed is:
1. A polyolefin stabilized against the deteriorating effects of light by having incorporated therein an effective amount of a light stabilizer of the formula:

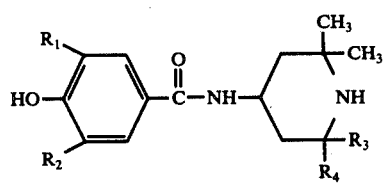

wherein $R_1$ and $R_2$ are each branch-chain alkyl of 3 to 8 carbon atoms and $R_3$ and $R_4$ are each alkyl of 1 to 4 carbon atoms.

2. A composition as defined in claim 1 wherein $R_1$ and $R_2$ are each t-butyl.

3. A composition as defined in claim 1 wherein $R_3$ and $R_4$ are each methyl.

4. A composition as defined in claim 1 wherein $R_1$ and $R_2$ are each t-butyl and $R_3$ and $R_4$ are each methyl.

5. A composition as defined in claim 1 wherein said polyolefin is polypropylene.

6. A composition as defined in claim 4 wherein said polyolefin is polypropylene.

7. A compound of the formula:

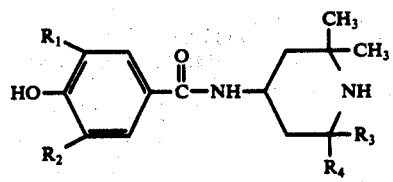

wherein $R_1$ and $R_2$ are each branch-chain alkyl of 3 to 8 carbon atoms and $R_3$ and $R_4$ are each alkyl of 1 to 4 carbon atoms.

8. A compound as defined in claim 7 wherein $R_1$ and $R_2$ are each t-butyl.

9. A compound as defined in claim 7 wherein $R_3$ and $R_4$ are each methyl.

10. A compound as defined in claim 7 wherein $R_1$ and $R_2$ are each t-butyl and $R_3$ and $R_4$ are each methyl.

* * * * *